United States Patent
Jahns et al.

(10) Patent No.: US 10,548,818 B2
(45) Date of Patent: Feb. 4, 2020

(54) KIT OF PARTS FOR PRODUCING A GLASS IONOMER CEMENT, PROCESS OF PRODUCTION AND USE THEREOF

(71) Applicant: 3M INNOVATIVE PROPERTIES COMPANY, St. Paul, MN (US)

(72) Inventors: Michael Jahns, Gilching (DE); Peter Braun, Penzing (DE); Robert Peez, Landsberg (DE); Markus Mikulla, Andechs-Frieding (DE); Rainer A. Guggenberger, Herrsching (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 70 days.

(21) Appl. No.: 15/745,565

(22) PCT Filed: Jul. 18, 2016

(86) PCT No.: PCT/US2016/042745
§ 371 (c)(1),
(2) Date: Jan. 17, 2018

(87) PCT Pub. No.: WO2017/015193
PCT Pub. Date: Jan. 26, 2017

(65) Prior Publication Data
US 2018/0214353 A1    Aug. 2, 2018

(30) Foreign Application Priority Data
Jul. 21, 2015  (EP) .................................... 15177624

(51) Int. Cl.
*A61K 6/08*      (2006.01)
*A61K 6/083*     (2006.01)
*A61K 6/00*      (2006.01)
*A61C 5/68*      (2017.01)

(52) U.S. Cl.
CPC .............. *A61K 6/0835* (2013.01); *A61C 5/68* (2017.02); *A61K 6/0008* (2013.01); *A61K 6/0038* (2013.01); *A61K 6/0085* (2013.01); *A61K 6/0088* (2013.01); *A61K 6/0091* (2013.01)

(58) Field of Classification Search
CPC .................................................. A61K 6/0835
See application file for complete search history.

(56) References Cited

U.S. PATENT DOCUMENTS

| | | | |
|---|---|---|---|
| 4,209,434 A | 6/1980 | Wilson | |
| 4,360,605 A | 11/1982 | Schmitt | |
| 4,376,835 A | 3/1983 | Schmitt | |
| 4,503,169 A * | 3/1985 | Randklev | A61K 6/083 106/35 |
| 4,569,954 A * | 2/1986 | Wilson | A61K 6/0017 106/35 |
| 4,738,722 A | 4/1988 | Ibsen | |
| 5,318,929 A | 6/1994 | Jana | |
| 5,520,922 A | 5/1996 | Gasser | |
| 5,558,701 A | 9/1996 | Patel | |
| 5,874,101 A | 2/1999 | Zhong | |
| 5,918,772 A | 7/1999 | Keller | |
| 5,944,419 A | 8/1999 | Streiff | |
| 5,965,632 A | 10/1999 | Orlowski | |
| 6,214,101 B1 | 4/2001 | Nakaseko | |
| 6,355,585 B1 | 3/2002 | Suzuki | |
| 6,437,019 B1 * | 8/2002 | Rusin | A61K 6/0017 523/117 |
| 6,719,834 B1 | 4/2004 | Braun | |
| 8,083,844 B2 | 12/2011 | Arita | |
| 2006/0187752 A1 | 8/2006 | Keller | |
| 2007/0072957 A1 | 3/2007 | Noguchi | |
| 2007/0088096 A1 * | 4/2007 | Mitra | A61K 6/0023 523/115 |
| 2007/0090079 A1 | 4/2007 | Kelller | |
| 2007/0254998 A1 | 11/2007 | Orlowski | |
| 2009/0214840 A1 * | 8/2009 | Eron | B41J 3/407 428/210 |

(Continued)

FOREIGN PATENT DOCUMENTS

| | | |
|---|---|---|
| DE | 10347900 | 5/2005 |
| EP | 0694298 | 1/1996 |

(Continued)

OTHER PUBLICATIONS

International search report for PCT International Application No. PCT/US2016/042745 dated Oct. 17, 2016, 6 pages.

(Continued)

*Primary Examiner* — Michael F Pepitone
(74) *Attorney, Agent, or Firm* — 3M Innovative Properties Compa

(57) ABSTRACT

The application relates to a kit of parts for preparing a glass ionomer composition for dental use, the kit comprising a Paste A and a Paste B, Paste A comprising water, acid-reactive inorganic filler C, non acid-reactive filler A, Paste B comprising water, polyacid, complexing agent, non acid-reactive filler B, the mean particle size of non acid-reactive filler B being larger than the mean particle size of non acid-reactive filler A, the water content of the composition obtained when mixing Paste A and Paste B being below 20 wt.-%. The application also relates to a device for storing such a kit of parts and the use of the kit of parts and/or the device for preparing a dental cement, dental filling material, dental core build up material or dental root channel filling material.

11 Claims, No Drawings

(56) References Cited

U.S. PATENT DOCUMENTS

2010/0063176 A1 3/2010 Kato
2012/0295214 A1 11/2012 Wang

FOREIGN PATENT DOCUMENTS

| EP | 1319386 | 6/2003 |
| EP | 2011469 | 1/2009 |
| EP | 2361601 | 8/2011 |
| GB | 907773 | 3/1959 |
| JP | 2002-275017 | 9/2002 |
| WO | WO 2005-016783 | 2/2005 |
| WO | WO 2007-104037 | 9/2007 |
| WO | WO 2009-061884 | 5/2009 |
| WO | WO 2010-123800 | 10/2010 |
| WO | WO 2011/081975 | 7/2011 |
| WO | WO 2012-101432 | 8/2012 |

OTHER PUBLICATIONS

Ilie, et al., Low-Shrinkage Composite for Dental Application, Dental Materials Journal 26(2) : 149-155, 2007.

* cited by examiner

KIT OF PARTS FOR PRODUCING A GLASS IONOMER CEMENT, PROCESS OF PRODUCTION AND USE THEREOF

FIELD OF THE INVENTION

The invention relates to a kit of parts for producing a glass ionomer cement (GIC), wherein the cement is obtainable by mixing two pastes.

BACKGROUND ART

Glass ionomer cements have been used for more than 30 years for dental restorative treatments.

Typically glass ionomer cements are reacted by mixing a powder part with a liquid part.

The powder component typically comprises as essential or important component an acid-reactive filler (e.g. a fluoro alumino silicate glass).

The liquid component typically comprises as essential components water, polycarboxylic acid and a complexing agent (e.g. tartaric acid) for adjusting the setting properties.

Main advantages of glass ionomer cements are said to be self-adhesion to tooth structure, fluoride release and the ability to be placed in one part (bulk-fill).

A disadvantage reported by some practitioners is the brittle nature and relatively low physical-mechanical properties of the glass ionomer cement compared to the physical-mechanical properties reported for resin-based composite filling materials.

Hence there have been various approaches to improve especially the flexural strength of glass ionomer cements.

E.g. it is reported that by increasing the overall content of polycarboxylic acid in comparison to the acid-reactive filler, the flexural strength can be improved.

However, by increasing the amount of polycarboxylic acid contained in the liquid part, the liquid part became too viscous making it nearly impossible to adequately mix the powder and liquid component.

To overcome this issue, it was suggested to put a part of the polycarboxylic acid in dry form into the powder component.

By doing this, however, it was realized that the storage stability of the product is sometimes negatively affected. Over time, humidity being present in the air may start to migrate into the powder component causing a glass ionomer reaction to start at least partially.

In order to overcome the susceptibility of the powder part to ambient humidity, encapsulating at least parts of the powder component was considered. It was also considered to add desiccants to the powder part. Another approach was to package the final product or at least the powder part into a humidity tight foil blister. This kind of packaging, however, is quite expensive and produces waste after use, which is not desired.

Further, encapsulating particles is often not easy and may affect the overall reactivity of the encapsulated powder. The same holds true for adding a desiccant.

Thus, there is still room for improvement especially with regard to the requirements to be fulfilled with respect to modern dental materials.

U.S. Pat. No. 4,376,835 (Schmitt et al.) describes a calcium aluminium fluorosilicate glass powder, wherein the calcium in the surface of the powder's particles is depleted. The glass powder may be prepared by surface treating calcium aluminium fluorosilicate powder particles with an acid which forms calcium salts, washing the calcium salts off the treated particles and drying the washed particles. Cements formed from the glass powder exhibit reduced periods of water sensitivity, while permitting sufficient time of processing.

U.S. Pat. No. 6,719,834 (Braun et al.) relates to a polyelectrolyte cement containing at least two reaction partners: a) at least one metal-cation-releasing compound and b) one or more polyelectrolyte capable of being converted into a solid state, wherein at least one of the polyelectrolytes is at least partially water soluble and wherein at least a part of the reaction partners (a) and/or (b) is coated with an organic surface-coating agent. The polyelectrolyte cement is stable in storage and can be easily mixed.

WO 2012/101432 relates to a mixture of a glass ionomer cement and zinc phosphate. Preferably, the composition comprises 40-95% by weight of fluorosilicate glass and 5-60% by weight of zinc oxide as acid-reactive components. The compositions are for use in the repair of human hard tissue, in particular as dental restorative materials and in orthopaedic surgery.

EP 2 011 469 describes a composition where hydroxyl apatite is added as a reactive component to glass ionomer cements.

EP 0 694 298 relates to the use of a preformed glass ionomer filler which comprises a powdery reaction product between a polyalkenoic acid and a fluoride glass. This filler can release fluoride ions. Whereas most examples refer to the use of the filler in resin containing, light-curing dental composition, there is also an example using this preformed glass ionomer in a carboxylate cement with Zinc oxide and Magnesium oxide as basic ingredients. Yet no examples were found with regards to the use of the pre-formed glass ionomer filler in conventional glass ionomers. Also it has to be understood, that the production of such a pre-formed glass ionomer fillers comprises several steps.

U.S. Pat. No. 5,318,929 discloses an apatite-containing glass ceramic, which can be used in particular in forming glass ionomer cement and biomaterials which improves manipulability and adhesion vis-a-vis known technical solutions of glass ionomer cements.

U.S. Pat. No. 4,738,722 describes a buffered glass ionomer cement for dental use, which contains as fillers fluoro boro phosphoro calcium alumino silicate, zinc oxide (5-20%) and titanium dioxide in place of about half the amount of zinc oxide.

U.S. Pat. No. 6,355,585 discloses a glass powder for glass ionomer cement having high mechanical strength, containing a glass powder for glass ionomer cement having a shape in which a major axis length is from 3 to 1,000 times a minor axis length, in a glass powder for glass ionomer cement. The composition of the glass powder described refers to an acid reactive fluoro alumino silicate glass.

U.S. Pat. No. 8,083,844 describes the use of hydroxyl apatite as filler in glass ionomer cements.

JP 2002-275017 describes a material for preparing dental glass ionomer cements. The powdery material comprises 10-50 wt.-% of fluoroaluminosilicate glass powder, less or equal than 10 wt.-% of a powder selected from certain oxides, with the balance of a powdery inert filler. Due to a reduced content of fluoroaluminosilicate glass powder (10 to 50 wt.-%), the glass ionomer cement is said to be excellent in temporarily adhesive and temporarily sealing use, i.e. has reduced mechanical properties. Compressive strength values in the range of less than 70 MPa are reported.

U.S. Pat. No. 5,520,922 (Gasser et al.) relates to a filling material for dental root canals comprising (A) 25-80 wt.-% glass ionomer cement containing (a) an aluminium fluorosilicate glass, (b) a certain polymeric polyacid, (c) water and (B) 25-75 wt.-% of a fluoride and/or oxide of heavy metal elements. In an example a cement powder is described containing 75 g of calcium tungstate, 25 g of calcium aluminium fluorosilicate glass and 4 g of pyrogenic silicic acid and pigments. The cement powder is mixed with an appropriate cement liquid resulting in a hardened product having a compressive strength of 90 MPa.

US 2007/0254998 (Orlowski et al.) describes a glass ionomer type dental cement composition with a first component comprising an aqueous solution of polymers of acrylic acid and a second substantially anhydrous component comprising alkaline glass flux in a medium comprising water soluble/miscible monomers or pre-polymers having at least one —OH group per molecule.

US 2007/0072957 A1 (Noguchi et al.) describes a dental paste glass ionomer cement composition comprising a first paste and a second paste, the first paste comprising i.a. 20 to 60 wt.-% of an unsaturated carboxylic acid polymer, 10 to 60 w.-% filler that is not reacted with the unsureated carboxylic acid polymer and is not in a monodisperse state in water, 0.1 to 10 wt.-% colloidal silica, 20 to 60 wt.-% water, the second paste comprising 50 to 85 wt.-% fluoroalumino silicate glass powder, 0.01 to 10 wt.-% thickening agent and 20 to 45 wt.-% water.

DESCRIPTION OF THE INVENTION

It is an object of the present invention to provide a glass ionomer cement, which can easily be mixed and shows adequate or improved physical properties after hardening (like flexural and/or compressive strength).

This object can be achieved by the kit of parts and the glass ionomer cement obtained when mixing the pastes of the kit of parts as described in the present text.

In one embodiment the present invention features a kit of parts for preparing a glass ionomer cement for dental use, the kit comprising a Paste A and a Paste B,
Paste A comprising
  water,
  acid-reactive inorganic filler C,
  non acid-reactive filler A,
Paste B comprising
  water,
  polyacid,
  complexing agent,
  non acid-reactive filler B,
  the mean particle size of non acid-reactive filler B being larger than the mean particle size of non acid-reactive filler A,
  the water content of the composition obtained when mixing Paste A and Paste B being below 20 or below 19 wt.-%.

In another embodiment, the invention relates to a process for producing a hardenable glass ionomer cement composition comprising the step of mixing Paste A and Paste B of the kit of parts as described in the present text.

The invention is also directed to a device for storing the kit of parts described in the present text, the device comprising two compartments, Compartment A and Compartment B, Compartment A containing Paste A and Compartment B containing Paste B, Paste A and Paste B being as described in the present text, Compartment A and Compartment B both comprising a nozzle or an interface for receiving an entrance orifice of a static mixing tip.

The invention is also directed to a hardened composition for dental use, the hardened composition being obtainable or obtained by mixing Paste A and Paste B of the kit of parts described in the present text to obtain a mixture, and letting the mixture harden.

Moreover, the invention features a method of using the kit of parts and the cement composition obtainable or being obtained by mixing the respective pastes as described in the present text for dental purposes, in particular as dental cement, dental filling material, dental core build up material or dental root channel filling material.

Unless defined differently, for this description the following terms shall have the given meaning:

A "dental composition" or a "composition for dental use" or a "composition to be used in the dental field" is any composition which can be used in the dental field. In this respect the composition should be not detrimental to the patients' health and thus free of hazardous and toxic components being able to migrate out of the composition. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

A "polymerizable component" is any component which can be cured or solidified e.g. by heating to cause polymerization or chemical crosslinking, or e.g. by radiation-induced polymerization or crosslinking, or e.g. using a redox initiator. A polymerizable component may contain only one, two, three or more polymerizable groups. Typical examples of polymerizable groups include unsaturated carbon groups, such as a vinyl group being present e.g. in a (methyl)acrylate group.

The cement composition described in the present text does not contain polymerizable components in an amount above about 0.5 or 1 wt.-% with respect to the whole composition. The cement composition described in the present text is essentially free of polymerizable components bearing (meth)acrylate groups.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth) acryloxy" group is a shorthand term referring to either an acryloxy group (i. e., $CH_2=CH-C(O)-O-$) and/or a methacryloxy group (i. e., $CH_2=C(CH_3)-C(O)-O-$).

An "initiator" is a substance being able to start or initiate the curing process of polymerizable components or monomers, e.g. redox/auto-cure chemical reaction or by a radiation induced reaction or by a heat induced reaction.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "d50/μm" with regard to particle size measurement means that 50% of the particles in the analyzed volume, the particles have a size below x μm. E.g., a particle size value of below 100 μm (d50) means that within the analyzed volume, 50% of the particles have a size below 100 μm.

"Paste" shall mean a soft, viscous mass of solids dispersed in a liquid. "Viscous" means a viscosity above about 3 Pa*s (at 23° C.).

A "liquid" means any solvent or liquid which is able to at least partially disperse or dissolve a component at ambient conditions (e.g. 23° C.). A liquid typically has a viscosity below about 10 or below about 8 or below about 6 Pa*s.

"Glass ionomer cement" or "GIC" shall mean a cement curing or hardening by the reaction between an acid-reactive glass and a polyacid in the presence of water.

"Resin modified glass ionomer cement" or "RM-GIC" shall mean a GIC containing in addition polymerizable component(s), an initiator system and typically 2-hydroxyl-ethyl-methacrylate (HEMA).

"Acid-reactive filler" shall mean a filler that chemically reacts in the presence of a (poly)acid leading to a hardening reaction.

"Non acid-reactive filler" shall mean a filler, which does not show a chemical reaction within 6 min or which only shows a reduced (i.e. time-delayed) hardening reaction, if mixed with a (poly)acid.

To distinguish an acid-reactive filler from a non acid-reactive filler the following test can or is to be conducted: A composition is prepared by mixing Part A with Part B in a mass ratio of 3 to 1, wherein: Part A contains: filler to be analyzed: 100 wt.-%; Part B contains: poly (acrylic acid co maleic acid) (Mw: about 20,000+/−3,000): 43.6 wt.-%, water: 47.2 wt.-%, tartaric acid: 9.1 wt.-%, benzoic acid: 0.1 wt.-%.

The filler is characterized as non-acid reactive, if within 6 min after preparing the above composition the shear stress is less than 50,000 Pa, if determined by conducting an oscillating measurement using a rheometer by applying the following conditions: using an 8 mm plate, 0.75 mm gap, at 28° C., frequency: 1.25 Hz, deformation: 1.75%.

"Cation reduced aluminosilicate glasses" shall mean a glass having a lower content of cations in the surface region of the glass particle compared with the inner region of the glass particle. These glasses react much slower upon contact with a solution of polyacrylic acid in water as compared to typical acid-reactive fillers. Examples of non acid-reactive fillers include quartz glass or strontium oxide based glasses. Further examples are given in the text below. Cation reduction can be achieved by a surface treatment of the glass particles. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution.

"Polyacid" or "polyalkenoic acid" shall mean a polymer having a plurality of acidic repeating units (e.g. more than 10 or more than 20 or more than 50). That is, the acidic repeating units are attached to or pending from the backbone of the polymer.

"Complexing agent" shall mean a low molecular agent comprising moieties and being able to form a complex with metal ions like calcium or magnesium; e.g. tartaric acid.

A "storage stable composition" is a composition which can be stored for an adequate period of time (e.g. at least about 12 months under ambient conditions) without showing significant performance issues (e.g. reduced flexural or compressive strength and/or which does not harden in the desired period of time (e.g. setting time greater than 6 min)) when used. A suitable test for determining the storage stability is given in the Example section below.

By "hardenable" or "curable" is meant that the composition can be cured or solidified, e.g. by conducting a glass ionomer cement reaction without the need for an additional curing system like chemical cross-linking, radiation-induced polymerization or crosslinking.

A composition is "essentially or substantially free of" a certain component, if the composition does not contain said component as an essential feature. Thus, said component is not wilfully added to the composition either as such or in combination with other components or ingredient of other components.

A composition being essentially free of a certain component usually contains the component in an amount of less than about 1 wt.-% or less than about 0.5 wt.-% or less than about 0.1 wt.-% or less than about 0.01 wt.-% with respect to the whole composition or material. The composition may not contain the said component at all. However, sometimes the presence of a small amount of the said component is not avoidable e.g. due to impurities contained in the raw materials used.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

Advantages/Effects

The kit of parts for producing a glass ionomer cement composition described in the present text has a couple of advantageous properties.

While conventional glass ionomer materials are usually offered as a powder/liquid system, a paste/paste system not only simplifies the hand-mixing procedure of the two components, it also enables the application of so-called automix systems, where the two components are mixed e.g. by using a static mixing device.

In order to be adequately mixed in an automix system, the respective pastes need to have an adequate viscosity. If the viscosity is too high, it may become difficult to press the pastes trough a static mixing cannula.

For adjusting the viscosity, typically a solvent like water is added to the composition. If, however, the water content becomes too high, a decrease of mechanical properties of the hardened composition may result.

Without wishing to be bound to a particular theory, it was found that reducing the overall water content in the composition close to a level of powder/paste glass ionomer materials may help to avoid a decline of mechanical properties like compressive strength.

A reduced water content typically goes along with an increase of the density of the respective pastes. According to the invention a low water content is achieved by different means:

Adding non acid-reactive filler to the paste containing the polyacid needed for the glass ionomer cement reaction (Paste B) allows the formulation of Paste B having a reduced water content.

Further, the paste containing the acid-reactive filler needed for the glass ionomer cement reaction (Paste A) should contain a non acid-reactive filler as well.

However, the particle size of the non acid-reactive filler contained in the paste containing the polyacid (Paste B) should be larger than the particle size of the non acid-reactive filler being contained in the paste containing the acid-reative filler (Paste A).

Otherwise the pastes might become too viscous due to the large surface of the filler particles. Mixing of the respective pastes using a static mixer might become difficult.

The particle size of non-acid reactive filler A in Paste A may also not be too small. If the particle size of that filler is too small, the surface of the filler particles will increase and thus making it more difficult to formulate a paste with a high filler but low water content.

It was also found that formulating the glass ionomer cement composition as a paste/paste system comprising a Paste A and a Paste B as described in the present text, with Paste A having a lower water content compared to Paste B may also help to facilitate the mixing process.

It was also found that the addition of non acid-reactive filler(s) to both pastes, Paste A and Paste B of the kit of parts described in the present text, may also help to facilitate the mixing process.

A mean particle size from one μm up to a few μm was found to be suitable for the polyacid containing paste (Paste B).

The kit of parts described in the present text thus enables the skilled person to provide a composition having superior handling properties.

The kit of parts described in the present text comprises two pastes. Upon mixing those two pastes, a composition in the form of a further paste is obtained. That composition hardens by a so-called glass ionomer cement reaction.

The kit of parts described in the present text comprises a Paste A.

Paste A contains water.

The water can be distilled, de-ionized, or plain tap water. Typically, de-ionized water is used.

The amount of water should be sufficient to provide adequate handling and mixing properties and to permit the transport of ions, particularly in the cement reaction.

Water is typically present in the following amount:
Lower limit: at least 5 or at least 7 or at least 9 wt.-%;
Upper limit: utmost 18 or utmost 16 or utmost 14 wt.-%;
Range: from 5 to 18 or from 7 to 16 or from 9 to 14 wt.-%;
 wt.-% with respect to the weight of Paste A.

If the amount of the water is too low, obtaining a workable consistency of the obtained paste might become difficult.

If the amount of water is too high, obtaining of a workable consistency of the obtained paste might become difficult, too. Further, it will become difficult to achieve the desired mechanical properties.

Paste A contains an acid-reactive inorganic filler C.

The nature and structure of the acid-reactive filler C is not particularly limited unless the desired result cannot be achieved. The acid-reactive filler C has to be able to undergo a glass-ionomer cement reaction.

According to one embodiment, the acid-reactive filler C can be characterized by at least one or more or all of the following parameters:
Mean particle size: about 3 to about 10 μm;
(d10/μm): from 0.5 μm to 3 μm; (d50/μm): from 2 μm to 7 μm; (d90/μm): from 6 μm to 15 μm.
pH value of a dispersion of 1 g filler stirred in 10 ml de-ionized water for 5 minutes: between 6 and 10 or between 7 and 10 or between 8 or 10.

If the mean particle size of the acid-reactive filler C is above the range outlined above, the consistency of the composition obtained when mixing the compositions contained in the parts of the kit of parts described in the present text will not be adequate and the desired mechanical properties might be negatively affected.

If the mean particle size of the acid-reactive filler C is below the range outlined above, the setting time will be too fast.

Suitable acid-reactive fillers C include metal oxides, metal hydroxides, hydroxyapatite or acid-reactive glasses.

Typical metal oxides include barium oxide, strontium oxide, calcium oxide, magnesium oxide, zinc oxide.

Typical metal hydroxides include calcium hydroxide, magnesium hydroxide, strontium hydroxide and mixtures thereof.

Typical acid-reactive glasses include aluminosilicate glasses and in particular fluoroaluminosilicate ("FAS") glasses.

FAS glasses are particularly preferred. The FAS glass typically contains a sufficient amount of elutable cations so that a hardened dental composition can be obtained when the glass is mixed with the other components of the hardenable composition.

The FAS glass also typically contains a sufficient amount of elutable fluoride ions so that the hardened composition will have cariostatic properties.

The glass can be made from a melt containing fluoride, silica, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Suitable FAS glasses will be familiar to those skilled in the art, and are available from a wide variety of commercial sources, and many are found in currently available glass ionomer cements such as those commercially available under the trade designations Ketac™-Molar or Ketac™-Fil Plus (3M ESPE Dental), and FUJI™ IX (G-C Dental Industrial Corp., Tokyo, Japan).

Fluoroaluminosilicate glasses can be prepared by fusing mixtures of silica, alumina, cryolite and fluorite.

Useful acid-reactive glasses can also be characterized by the Si/Al ratio. Fillers having a Si/Al ratio (by wt.-%) of below 1.5 or 1.4 or 1.3 were found to be useful. Suitable acid-reactive fillers are also commercially available from e.g. Schott AG (Germany) or Speciality Glass (US).

Mixtures of acid-reactive fillers C can be used, if desired.

The acid-reactive filler C is typically present in the following amount:
Lower limit: at least 20 or at least 30 or at least 40 wt.-%;
Upper limit: utmost 90 or utmost 85 or utmost 80 wt.-%;
Range: from 20 to 90 or from 30 to 85 or from 40 to 80 wt.-%, wt.-% with respect to the weight of Paste A.

If the amount of the acid-reactive filler is too high, the pastes of the kit of parts described in the present text cannot be adequately mixed. Further, obtaining an adequate consistency and acceptable mechanical properties of the resulting composition might become difficult.

If the amount of the acid-reactive filler is too low, a suitable paste cannot be obtained by mixing the respective pastes of the kit of parts described in the present text. Further, the mechanical properties might become inferior.

Paste A contains a non acid-reactive filler A.

A non acid-reactive filler is a filler, which either does not cure in a glass ionomer cement reaction at all, if combined with a polyacid in the presence of water, or only shows a delayed curing reaction.

A more precise definition of non acid-reactive filler is given above.

The nature and structure of the non acid-reactive filler A is not particularly limited, either unless the desired result cannot be achieved.

The non-acid reactive filler A is preferably an inorganic filler.

The non-acid reactive filler A should be non-toxic and suitable for use in the mouth of a human being.

The non-acid reactive filler A can be radiopaque or radiolucent.

According to one embodiment, the non acid-reactive filler A can be characterized by at least one or more or all of the following parameters:
Mean particle size: about 10 nm to about 500 nm
Containing no particles larger than 2 μm.
pH value of a dispersion of 1 g filler stirred in 10 ml de-ionized water for 5 minutes: between 4 and 7.

If the mean particle size of the non acid-reactive filler A is above the range outlined above, the consistency of the obtained paste might not be adequate and in addition it might become difficult to obtain the desired mechanical properties.

If the mean particle size of the non acid-reactive filler A is below the range outlined above, the desired consistency of the obtained paste might not be adequate.

Examples of suitable non acid-reactive fillers A are naturally occurring or synthetic materials including, but not limited to: kaolin; silica particles (e.g., submicron pyrogenic silicas such as those available under the trade designations "AEROSIL", including "OX 50," "130," "150" and "200", silicas from Degussa AG, Hanau, Germany and HDK, including "H15", "H20", "H2000" from Wacker, Munich, Germany and CAB-O-SIL M5 silica from Cabot Corp., Tuscola, Ill.), alumina, titania and zirconia particles.

Mixtures of these non-acid-reactive fillers A are also contemplated.

Sometimes, the non acid-reactive filler A is provided as a dispersion or sol of particles in a liquid (e.g. water).

If the filler is provided as an aqueous dispersion or sol, the amount of water in the aqueous dispersion or sol has to be taken into account when the amount of water and filler in the composition is calculated or determined.

Suitable non acid-reactive fillers A are also commercially available as aqueous dispersions from e.g. Obermeier, Bad Berleburg, Germany under the trade name Levasil™, including type "50/50%", wherein the % value indicates the filler content.

The surface of the particles of the non acid-reactive fillers A is usually not surface treated, e.g. with silanes.

According to one embodiment, the non acid-reactive filler A is selected from silica, (alumo-)silicates, alumina and mixtures thereof.

The non acid-reactive filler A is typically present in the following amounts:
Lower limit: at least 1 or at least 3 or at least 5 wt.-%;
Upper limit: utmost 50 or utmost 40 or utmost 30 wt.-%;
Range: from 1 to 50 or from 3 to 40 or from 5 to 30 wt.-%. wt.-% with respect to the weight of Paste A.

Paste A can typically be characterized by either, more or all of the following features:
Viscosity: from 200 to 50,000 Pa*s (28° C.; 10 mm diameter, shear rate: $1\ s^{-1}$);
Density: from 1.9 to 2.8 $g/cm^3$;
pH value: from 7 to 10 or 8 to 10 (determined with a pH electrode for 1 g Paste A being dispersed in 10 ml de-ionized water and stirred for 5 minutes).

The kit of parts described in the present text comprises a Paste B.

Paste B contains water. The water contained in Paste B is as described for Paste A.

Water is typically present in the following amount:
Lower limit: at least 7 or at least 9 or at least 11 wt.-%;
Upper limit: utmost 20 or utmost 19 or utmost 18 wt.-%;
Range: from 7 to 20 or from 9 to 19 or from 11 to 18 wt.-%;
wt.-% with respect to the weight of Paste B.

Paste B contains a polyacid.

The nature and structure of the polyacid is not particularly limited, either, unless the desired result cannot be achieved. However, the polyacid should have a molecular weight sufficient to provide good storage, handling, and mixing properties, as well as to yield good material properties in the glass ionomer material.

According to one embodiment, the polyacid can be characterized by at least one or more or all of the following parameters:
Being a solid (at 23° C.);
Molecular weight (Mw): from about 2,000 to about 250,000 or from about 5,000 to about 100,000 (evaluated against a polyacrylic acid sodium salt standard using gel permeation chromatography).

If the molecular weight of the polyacid is too high, obtaining a workable consistency of the obtained paste when mixing the compositions contained in the kit of parts described in the present text might become difficult. Further, preparation of the compositions might become difficult. In addition, the obtained mixture or composition might become too sticky (i.e. adheres to the dental instrument used for application).

If the molecular weight of the polyacid is too low, the viscosity of the obtained paste might become too low and the mechanical properties inferior.

Typically, the polyacid is a polymer having a plurality of acidic repeating units.

The polyacid to be used for the cement composition described in the present text is substantially free of polymerizable groups.

The polyacid need not be entirely water soluble, but typically it is at least sufficiently water-miscible so that it does not undergo substantial sedimentation when combined with other aqueous components.

The polyacid is hardenable in the presence of, for example, an acid-reactive filler and water, but does not contain ethylenically unsaturated groups.

That is, the polyacid it is a polymer obtained by polymerising an unsaturated acid. However, due to the production process, a polyacid might still contain unavoidable traces of free monomers (e.g. up to 1 or 0.5 or 0.3 wt.-% with respect to the amount of monomers used).

Typically, the unsaturated acid is an oxyacid (i.e., an oxygen containing acid) of carbon, sulfur, phosphorous, or boron. More typically, it is an oxyacid of carbon.

Suitable polyacids include, for example, polyalkenoic acids such as homopolymers and copolymers of unsaturated mono-, di-, or tricarboxylic acids.

Polyalkenoic acids can be prepared by the homopolymerization and copolymerization of unsaturated aliphatic carboxylic acids, e.g., acrylic acid, methacrylic acid, itaconic acid, maleic acid, glutaconic acid, aconitic acid, citraconic acid, mesaconic acid, fumaric acid, and tiglic acid.

Suitable polyacids also include alternating copolymers of maleic acid and ethylene (e.g. in a molar one to one ratio).

Suitable polyacids are also described in the following documents: U.S. Pat. No. 4,209,434 (Wilson et al.), U.S. Pat. No. 4,360,605 (Schmitt et al.). The content of these documents with respect to the description of the polyacid is herewith incorporated by reference.

Suitable polyacids are also included as aqueous solutions in the liquid component of commercially available products from e.g. 3M ESPE (e.g. Ketac™ Fil Plus Handmix) or GC Company (e.g. Fuji™ IX GP Handmix).

The amount of polyacid should be sufficient to react with the acid-reactive filler and to provide an ionomer composition with desirable hardening properties.

The polyacid is typically present in the following amount:
Lower limit: at least 3 or at least 5 or at least 10 wt.-%;
Upper limit: utmost 70 or utmost 60 or utmost 50 wt.-%;
Range: from 3 to 70 or from 5 to 60 or from 10 to 50 wt.-%.
wt.-% with respect to the weight of Paste B.

If the amount of the polyacid is too high, obtaining a workable consistency of the obtained paste when mixing the compositions contained in the kit of parts described in the present text might become difficult. Further, preparation of the compositions might become difficult. In addition, the obtained mixture or composition might become too sticky (i.e. adheres to the dental instrument used for application).

If the amount of the polyacid is too low, obtaining a workable consistency of the obtained paste when mixing the compositions contained in the kit of parts described in the present text might become difficult, either. Further, it will become difficult to achieve the desired mechanical properties.

Paste B contains a non acid-reactive filler B.

The non acid-reactive filler B contained in Paste B can be the same or a different material as the non acid-reactive filler A described for Paste A. However, the mean particle size of the non acid-reactive filler B contained in Paste B is larger than the mean particle size of the non-acid reactive filler A contained in Paste A.

According to one embodiment, the non acid-reactive filler B can be characterized by at least one or more or all of the following parameters:
Mean particle size: about 1 to about 10 µm;
(d10/µm): from 0.2 µm to 2 µm; (d50/µm): from 0.5 µm to 5 µm; (d90/µm) from 1 µm to 15 µm;
pH value of a dispersion of 1 g filler stirred in 10 ml de-ionized water for 5 minutes: between 4 and 7 or 4 to 6.

Examples of suitable non acid-reactive fillers B are naturally occurring or synthetic materials including, but not limited to: quartz; nitrides (e.g., silicon nitride); glasses derived from, e.g., Zr, Sr, Ce, Sb, Sn, Ba, Zn, and Al; borosilicate glass; kaolin; silica particles (e.g. quartz glass or pyrogenic silica of suitable particle size), alumina, titania and zirconia particles.

According to one embodiment, the non acid-reactive filler B is selected from quartz, titanium oxide, silica, alumina, aluminosilicates and mixtures thereof.

If desired, the surface of the particles of the acid-reactive filler B can be surface treated. Suitable surface-treating agents include silanes, e.g. trimethoxysilanes carrying an organic functional group to modify the chemical properties of the particles. Suitable silanes are e.g. silanes to modify the acidic properties (carrying amino groups or carrying carboxylic acid groups) or silanes to modify the hydrophobicity/hydrophilicity (carrying an alkane chain or carrying a polyethylene glycol chain).

The non acid-reactive filler B is typically present in the following amounts:
Lower limit: at least 5 or at least 10 or at least 15 wt.-%;
Upper limit: utmost 60 or utmost 50 or utmost 40 wt.-%;
Range: from 5 to 60 or from 10 to 50 or from 15 to 40 wt.-%.
wt.-% with respect to the weight of Paste B.

Paste B contains a complexing agent.

The nature and structure of the complexing or chelating agent is not particularly limited, either unless the desired result cannot be achieved.

The complexing agent can be characterized by at least one or more or all of the following parameters:
Solubility: soluble in water (at least 50 g/1 water at 23° C.);
Molecular weight: from 50 to 500 g/mol, or from 75 to 300 g/mol.

Specific examples of the complexing agent include tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof.

Further examples can be found e.g. in U.S. Pat. No. 4,569,954 (Wilson et al.). The content of this document is herewith incorporated by reference.

The complexing agent is typically added to that paste containing the polyacid only, i.e., to Paste B.

The complexing agent is typically present in the following amount:
Lower limit: at least 0.1 or at least 1.0 or at least 1.5 wt.-%;
Upper limit: utmost 12 or utmost 10 or utmost 8 wt.-%;
Range: from 0.1 to 12 or from 1.0 to 10 or from 1.5 to 8 wt.-%.
wt.-% with respect to the weight of the Paste B.

Paste B can typically be characterized by either, more or all of the following features:
Viscosity: from 1000 to 50000 Pa*s (28° C.; 10 mm diameter; shear rate: 1 s$^{-1}$);
Density: from 1.5 to 2.0 g/cm$^3$;
pH value: from 1 to 4 (determined with a pH electrode for 1 g paste being dispersed in 10 ml de-ionized water and stirred for about 5 minutes).

Either Paste A or Paste B or Paste A and Paste B of the kit of parts described in the present text can also contain solvent(s).

Adding solvent(s) or co-solvent(s) may help to adjust the viscosity and consistency of the composition.

Examples of solvent(s) which can be used include alcohols (e.g. methanol, ethanol, propanol), polyalcohols/polyols (e.g. ethylene glycol, glycerol) and mixtures thereof.

Either Paste A or Paste B or Paste A and Paste B of the kit of parts described in the present text can also contain additives.

Additives which might be present include indicator(s), dye(s), pigment(s), viscosity modifier(s), surfactant(s), buffering agent(s), stabilizer(s), preservative agent(s) (e.g., benzoic acid).

Combination of any of the above additives may also be employed. The selection and amount of any one such additive can be selected by one of skill in the art to accomplish the desired result without undue experimentation.

There is no need for those component(s) to be present, however, if present, the individual component is typically present in an amount of less than 5 wt.-% or less than 3 wt.-% or less than 1 wt.-% with respect to the weight of the respective Paste (A or B).

Useful ranges of those component(s) include from 0.01 to 5 wt.-% or from 0.05 to 3 wt.-% or from 0.1 to 1 wt.-%, wt.-% with respect to the weight of the respective Paste (A or B).

Typically neither Paste A nor Paste B or nor Paste A and Paste B of the kit of parts described in the present text do contain either of the following components alone or in combination:
a) HEMA in an amount above 1 wt.-% or above 0.5 wt.-%;
b) polymerizable component(s) in an amount above 1 wt.-% or above 0.5 wt.-%;
c) initiator component(s) suitable to cure polymerizable component(s) or monomer(s) in an amount above 1 wt.-% or above 0.5 wt.-%;
d) inhibitior(s) like methoxyphenol or 3,5-Di-tert-butyl-4-hydroxytoluol in an amount above 1 wt.-% or above 0.5 wt.-%;
e) desiccant(s) like zeolithe(s) in an amount above 1 wt.-% or above 0.5 wt.-%.

Thus, the composition obtained when mixing the powder and liquid part of the kit of parts described in the present text is not a so-called resin-modified glass ionomer cement (RM-GIC) and thus does not contain a curing system based on polymerization.

In particular, the cement composition described in the present text does not contain a redox-initiator system or a thermally induced initiator system or a radiation induced initiator system.

In particular the cement composition described in the present text does not contain the following components:
(a) and (b),
(b) and (c),
(a), (b) and (c),
(b), (c) and (d),
(a), (b), (c) and (d)
in an amount above 1 wt.-% or above 0.5 wt.-% or above 0.1 wt.-% with respect to the weight of the whole composition.

That is, the cement composition described in the present text is typically essentially free of either of these components alone or in combination.

The glass ionomer cement composition obtained when mixing Paste A and Paste B of the kit of parts described in the present text can typically be characterized as follows:
Comprising water in the following amounts:
Lower limit: at least 6 or at least 8 or at least 10 wt.-%;
Upper limit: utmost 20 or utmost 19 or utmost 18 wt.-%;
Range: from 6 to 20 or from 8 to 19 or from 10 to 18 wt.-%.
Comprising the non acid-reactive filler A in the following amounts:
Lower limit: at least 1 or at least 2 or at least 3 wt.-%;
Upper limit: utmost 40 or utmost 30 or utmost 20 wt.-%;
Range: from 1 to 40 or from 2 to 30 or from 3 to 20 wt.-%.
Comprising the non acid-reactive filler B in the following amounts:
Lower limit: at least 2 or at least 4 or at least 6 wt.-%;
Upper limit: utmost 50 or utmost 40 or utmost 30 wt.-%;
Range: from 2 to 50 or from 4 to 40 or from 6 to 30 wt.-%.
Comprising the acid-reactive filler C in the following amounts:
Lower limit: at least 10 or at least 20 or at least 30 wt.-%;
Upper limit: utmost 80 or utmost 75 or utmost 70 wt.-%;
Range: from 10 to 80 or from 20 to 75 or from 30 to 70 wt.-%.
Comprising the polyacid in the following amounts:
Lower limit: at least 2 or at least 4 or at least 7 wt.-%;
Upper limit: utmost 50 or utmost 40 or utmost 30 wt.-%;
Range: from 2 to 50 or from 4 to 40 or from 7 to 30 wt.-%.
Comprising complexing agent in the following amounts:
Lower limit: at least 0.1 or at least 0.5 or at least 1.0 wt.-%;
Upper limit: utmost 10 or utmost 8 or utmost 6 wt.-%;
Range: from 0.1 to 10 or from 0.5 to 8 or from 1.0 to 6 wt.-%.
With respect to the above amount, the wt.-% refer to the weight of the whole composition obtained when mixing the pastes of the kit of parts.

The amount of fillers A, B and C contained in the composition obtained when mixing Paste A and Paste B is typically above 50 or above 55 or above 60 wt.-%.

The water content of the composition obtained when mixing Paste A and Paste B is below 20 or below 19 or below 18 or below 17 wt.-%.

A high filler content combined with a low water content typically helps to improve mechanical properties of the hardened composition like compressive strength.

The invention also relates to a composition obtained when mixing the respective pastes of the kit of parts described in the present text.

According to one embodiment the cement composition obtained or obtainable by mixing the two pastes of the kit of parts described in the present text fulfils at least one or both of the following parameters before or during hardening:
Setting time: within about 5 or 4 or 3 min determined according to EN-ISO 9917-1:2007;
Working time: within about 4 or 3 or 2 or 1 min determined according to EN-ISO 9917-1:2007;
Being storage stable.

If desired, the setting time and curing behaviour can be determined as described in more detail in the Example section below.

The cement composition described in the present text typically has a sufficient working time allowing the practitioner not only to adequately mix the composition but also to apply the composition to the surface of a crown, bridge, root canal or prepared tooth.

Further, the cement composition described in the present text has an adequate setting time, which is time saving for the practitioner and convenient for the patient.

According to another embodiment the cement composition obtained or obtainable by mixing the two pastes of the kit of parts described in the present text fulfils at least one or more, sometimes all of the following parameters after hardening:

Flexural strength: above about 20 or above about 25 MPa determined according to EN-ISO 9917-2:2010 with the proviso that for covering the composition a glass slab is used instead of a foil;

Compressive strength: above about 100 or above about 120 or above about 150 MPa determined according to EN-ISO 9917-1/2007 with the proviso that for covering the composition a glass slab is used instead of a foil;

If desired, these parameters can be determined as described in the Example section below.

Compared to state of the art glass ionomer cements available on the market, the cement composition described in the present text can easily be mixed and has adequate mechanical properties like compressive strength without affecting other important parameters like setting time.

According to one embodiment, the invention is directed to a kit of parts as described in the present text with:

Paste A comprising:
  water in an amount from 10 to 13 wt.-%,
  acid-reactive inorganic filler C in an amount from 65 to 80 wt.-%, the acid-reactive inorganic filler C having a mean particle size in the range of 3 to 10 µm and being selected from metal oxides, acid-reactive glasses and mixtures thereof.
  the non acid-reactive filler A in an amount from 6 to 20 wt.-%, the non acid-reactive filler A having a mean particle size in the range of 10 to 500 nm and being selected from silica, alumina and mixtures thereof, Paste B comprising:
  water in an amount from 12 to 19 wt.-%,
  the polyacid in an amount from 35 to 50 wt.-%,
  the complexing agent in an amount from 3 to 8 wt.-%,
  the non acid-reactive filler B in an amount from 25 to 40 wt.-%, the non acid-reactive filler B having a mean particle size in the range of 1 to 10 µm and being selected from quartz, kaolin, silica, alumina and mixtures thereof, wt.-% with respect to the weight of the respective Paste A or Paste B, neither Paste A nor Paste B comprising polymerizable component(s) in an amount above 1.0 wt.-% with respect to the weight of the composition obtained when mixing Paste A and Paste B, Paste A having a density in the range of 1.9 to 2.8 g/cm$^3$, Paste B having a density in the range of 1.5 to 2.0 g/cm$^3$, and/or Paste A having a viscosity in the range of 200 to 50,000 Pa*s, and Paste B having a viscosity in the range of 1,000 to 50,000 Pa*s, the viscosity being measured at 28° C. with a plate diameter of 10 mm at a shear rate of 1 s$^{-1}$.

According to another embodiment, the invention is directed to a kit of parts as described in the present text with:

Paste A comprising:
  water in an amount from 10 to 15 wt.-%,
  acid-reactive inorganic filler C in an amount from 65 to 80 wt.-%, the acid-reactive inorganic filler C having a mean particle size in the range of 3 to 10 µm and being selected from metal oxides, acid-reactive glasses and mixtures thereof.
  the non acid-reactive filler A in an amount from 6 to 20 wt.-%, the non acid-reactive filler A having a mean particle size in the range of 10 to 500 nm and being selected from silica, alumina and mixtures thereof, Paste B comprising:
  water in an amount from 11 to 19 wt.-%,
  polyacid in an amount from 15 to 30 wt.-%,
  complexing agent in an amount from 2 to 8 wt.-%,
  non acid-reactive filler B in an amount from 40 to 60 wt.-%, the non acid-reactive filler B having a mean particle size in the range of 1 to 10 µm and being selected from quartz, kaolin, silica, alumina and mixtures thereof, wt.-% with respect to the weight of the respective Paste A or Paste B, neither Paste A nor Paste B comprising polymerizable component(s) in an amount above 1.0 wt.-% with respect to the weight of the composition obtained when mixing Paste A and Paste B, Paste A having a density in the range of 1.9 to 2.8 g/cm$^3$, Paste B having a density in the range of 1.5 to 2.0 g/cm$^3$, and/or Paste A having a viscosity in the range of 200 to 50,000 Pa*s, and Paste B having a viscosity in the range of 1,000 to 50,000 Pa*s, the viscosity being measured at 28° C. with a plate diameter of 10 mm at a shear 5 rate of 1 s$^{-1}$.

The pastes of the kit of part described in the present text can be produced by simply mixing the individual components of the respective pastes.

If needed, the filler particles can be milled to the desired particle size using equipment known to the skilled person like ball mills.

Mixing can be accomplished either by hand or with a mechanical device like a mixer or kneading machine. The mixing duration can vary depending on the composition and the mixing device and should be sufficiently long to obtain a homogeneous paste.

The kit of parts described in the present text can be provided to the practitioner in different embodiments.

The pastes may be contained in separate sealable vessels (e.g. made out of plastic or glass).

For use, the practitioner may take adequate portions of the pasty components from the vessels and mix the portions by hand on a mixing plate.

According to a preferred embodiment, the pastes are contained in separate compartments of a storing device.

The storing device typically comprises two compartments for storing the respective pastes, each compartment being equipped with a nozzle for delivering the respective paste. Once delivered in adequate portions, the pastes can then be mixed by hand on a mixing plate.

According to another preferred embodiment, the storing device has an interface for receiving a static mixing tip. The mixing tip is used for mixing the respective pastes. Static mixing tips are commercially available e.g. from Sulzer-Mixpac company. Suitable storing devices include cartridges, syringes and tubes.

The storing device typically comprises two housings or compartments having a front end with a nozzle and a rear end and at least one piston movable in the housing or compartment.

Cartridges which can be used are described e.g. in US 2007/0090079 or U.S. Pat. No. 5,918,772, the disclosure of which is incorporated by reference. Some of the cartridges which can be used are commercially available e.g. from SulzerMixpac AG (Switzerland). Static mixing tips which can be used are described e.g. in US 2006/0187752 or in U.S. Pat. No. 5,944,419, the disclosure of which is incorporated by reference. Mixing tips which can be used are commercially available from SulzerMixpac AG (Switzerland), as well.

Other suitable storing devices are described e.g. in WO 2010/123800 (3M), WO 2005/016783 (3M), WO 2007/104037 (3M), WO 2009/061884 (3M), in particular the device shown in FIG. 14 or WO 2009/061884 (3M), in particular the device shown in FIG. 14. The content of these references is herewith incorporated by reference, as well.

Alternatively, but less preferred, paste/paste compositions described in the present text can be provided in two individual syringes and the individual pastes can be mixed by hand prior to use.

Thus, the invention is also directed to a device for storing the kit of parts described in the present text, the device comprising two compartments, Compartment A and Compartment B, Compartment A containing Paste A and Compartment B containing Paste B, Paste A and Paste B being as described in the present text, Compartment A and Compartment B both comprising a nozzle or an interface for receiving an entrance orifice of a static mixing tip.

The mixing ratio of Paste A and Paste B is typically from 3:1 to 1:2 with respect to volume, preferably from 2:1 to 1:2.

Alternatively, the mixing ratio of Paste A and Paste B is typically from 6:1 to 1:1 with respect to weight, preferably from 4:1 to 1:1.

The composition obtained or obtainable when mixing the respective pastes is in particular useful as or for producing a dental cement, dental filling material, dental core build up material or as dental root channel filling material.

A typical application comprises the following steps:
a) mixing Paste A and Paste B to obtain a hardenable composition,
b) applying the hardenable composition to the surface of hard dental tissue,
c) letting the hardening composition harde n.

The kit of parts described in the present text typically contains in addition an instruction for use.

The instruction for use typically contains hints how to store the kit of parts, mix the pastes of the kit of parts and/or how to apply the composition obtained by mixing the pastes to the surface of hard dental tissue.

All components used in the dental composition of the invention should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Density

The density of the pastes was measured by filling the pastes into a container of defined volume and by weighing the container with and without paste. The weight difference divided by the defined volume yields the density of the paste. It was taken care that during filling of the container the inclusion of air bubbles was minimized. Also, one repeat determination was performed and the two results were averaged.

Viscosity

The viscosity of the pastes was measured with a Physica MCR 300 rheometer from Anton Paar. The measurement was performed in a rotating disc on disc setup with the diameter being 10 mm. The temperature was set to 28° C., the gap to 2 mm and the shear rate to 1 s$^{-1}$.

Five values taken from 30 to 35 seconds into the measurement were averaged. Repeat determination was done for all samples.

Compressive Strength (CS)

Measurement of the compressive strength was carried out according to the EN-ISO 9917-1:2007 with the proviso that for covering the composition a glass slab is used instead of a foil.

Cylindrical specimens with a diameter of 4 mm and a height of 6 mm were used. Specimens of the materials were prepared at room temperature and 50% relative humidity using split moulds. The moulds were placed on microscope slides and thoroughly filled with the mixed material to avoid incorporation of air bubbles. The filled moulds were immediately covered with another glass slab and fixed in a screw clamp with slight pressure to extrude excess material. The whole assembly was stored at 36° C. and at least 95% relative humidity. 1 h after start of mixing the specimens were removed from the moulds and immediately placed in water at 36° C. 6 specimens were prepared for each material. Materials were measured 24 h after start of mixing. The exact diameter of each specimen was measured prior to the measurement. The strength of the specimen was measured by applying a compressive load using a Zwick universal testing machine (Zwick GmbH & Co. KG, Ulm, Germany) operating at a crosshead speed of 1 mm/min. Results were reported as an average of 6 replications.

Flexural Strength (FS)

Flexural strength was measured based on EN ISO 9917-2:2010 with the proviso that for covering the composition a glass slab is used instead of a foil;

The specimens were prepared as described for the compressive strength test above, except that rectangular-shaped split moulds with dimensions 25 mm×2 mm×2 mm were used to prepare the samples. The specimens were subjected to a 3 point bend on supports 20 mm apart at a crosshead speed of 1 mm/min.

pH Value Measurement

If desired, the pH value of the filler components and pastes can be determined as follows: 1.0 g filler or paste is dispersed in 10 ml de-ionized water and stirred for about 5 min. A calibrated pH electrode is dipped into the suspension and the pH value is determined during stirring.

Storage Stability

If desired, storage stability can be determined according to the following process: The pastes were stored for a given period of time under the following conditions: about 50% relative humidity at 23° C. After storage the composition obtained when mixing the pastes were analysed for mechanical performance. If the mechanical properties (e.g. flexural strength, compressive strength) do not deviate by more than +/−20%, the composition is considered storage stable.

Particle Size (Suitable for Non Acid-Reactive Filler B and Acid-Reactive Filler C, Micro-Sized Particles)

The particle size distribution including the mean particle size was determined with a Cilas 1064 (FA. Quantacrome) particle size detection device. During the measurement, ultrasonic was used to accurately disperse the sample.

Particle Size (Suitable for Non Acid-Reactive Filler A, Nano-Sized Particles)

Particle size measurements were made using a light scattering particle sizer equipped with a red laser having a 633 nm wavelength of light (obtained under the trade designation "ZETA SIZER—Nano Series, Model ZEN3600" from Malvern Instruments Inc., Westborough, Mass.). Each sample was analyzed in a one-centimeter square polystyrene sample cuvette. The sample was diluted 1:100, e.g. 1 g of sample was given to 100 g of de-ionized water and mixed. The sample cuvette was filled with about 1 gram of diluted sample. The sample cuvette was then placed in the instrument and equilibrated at 25° C. The instrument parameters were set as follows: dispersant refractive index 1.330, dispersant viscosity 0.8872 mPa*s, material refractive index 1.43, and material absorption value 0.00 units. The automatic size-measurement procedure was then run. The instrument automatically adjusted the laser-beam position and attenuator setting to obtain the best measurement of particle size.

The light scattering particle-sizer illuminated the sample with a laser and analyzed the intensity fluctuations of the light scattered from the particles at an angle of 173 degrees. The method of Photon Correlation Spectroscopy (PCS) was used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

In the scope of this document the Z-average size is referred to as "mean particle size".

Molecular Weight

If desired, the molecular weight (Mw) can be determined by gel permeation chromatography (GPC) against a polyacrylic acid sodium salt standard.

In particular the following equipment was found to be useful: PSS SECurity GPC System equipped with 2*PSS Suprema 3000A, 8*300 mm, 10 μm columns; eluent: 84 mM Na2HPO4+200 ppm NaN3; flux rate: 1 ml/min.

Materials

TABLE 1

| Name | Description |
| --- | --- |
| Levasil ™ 50/50% | Non acid-reactive filler A; from Obermeier, dispersion of silica particles in water at about 50 wt.-%; mean particle size of silica particles: 114 nm |
| Levasil ™ 200/40% | Non acid-reactive filler A; from Obermeier, dispersion of silica particles in water at about 40 wt.-%; mean particle size of silica particles: 34 nm |
| Levasil ™ 300/30% | Non acid-reactive filler A; from Obermeier, dispersion of silica particles in water at about 30 wt.-%; mean particle size of silica particles: 18 nm |
| ionomer glass powder | Acid-reactive filler C; Powder component of Ketac ™ Molar (from 3M ESPE Dental); mean particle size: 3.84 μm, d10: 0.87 μm, d50: 2.73 μm, d90: 8.80 μm. |
| quartz powder | Non acid-reactive filler B; mean particle size: 1.16 μm, d10: 0.41 μm, d50: 0.98 μm, d90: 2.06 μm. |
| kaolin powder, Huber 70C | Non acid-reactive filler B; from Huber; mean particle size: 5.18 μm, d10: 0.91 μm, d50: 3.59 μm, d90: 12.24 μm. |
| tartaric acid | Complexing agent |
| polyacid | acrylic acid/maleic acid co-polymer (1:1 co-polymer), Mw = 20,000 |
| methyl cellulose | Thickening agent; viscosity 8,000 mPa * s |
| p-toluenesulfonic acid monohydrate | purity 98% |
| silane (X-12-967C) | from Shin-Etsu, silane with succinic acid anhydride residue |

TABLE 1-continued

| Name | Description |
| --- | --- |
| ammonia solution | 25% solution in water |
| isopropyl alcohol | 2-propanol; purity >99.7% |

Surface Treatment of Quartz (Non Acid-Reactive Filler B)

7.5 mg p-toluenesulfonic acid monohydrate, 2.3 g de-ionized water, 2.3 g isopropyl alcohol and 4.5 g silane (X-12-967C) were mixed and stirred for 1 hour at 25° C. The resulting solution had a pH value of 3. 150 g quartz powder and 200 g isopropyl alcohol were mixed. Ammonia solution (25%) was added drop-wise to the mixture until a pH value of 8-9 was reached. The viscosity of the mixture increased upon addition of ammonia, so another 50 g of isopropyl alcohol were added. After stirring for 1 hour at 25° C., the silane solution was added and stirred for another 3 hours at 25° C. The mixture was dried in a rotary evaporator. The dry substance was sieved (500 μm) and the silanation was fixed in a rotary evaporator (standard pressure, 100° C., 1 hour).

Paste A1

A composition containing 1.00 g Levasil™ 50/50% and 3.00 g ionomer glass powder (Ketac™ Molar) was prepared. A homogeneous mixture was obtained by mixing with a magnetic stirrer.

Paste A2

A composition containing 3.20 g Levasil™ 50/50% and 11.20 g ionomer glass powder (Ketac™ Molar) was prepared. A homogeneous mixture was obtained by hand-mixing with a spatula.

Paste A3

A composition containing 0.80 g Levasil™ 200/40% and 2.80 g ionomer glass powder (Ketac™ Molar) was prepared. A homogeneous mixture was obtained by mixing with a magnetic stirrer.

Paste A4

A composition containing 0.80 g Levasil™ 300/30% and 2.80 g ionomer glass powder (Ketac™ Molar) was prepared. A homogeneous mixture was obtained by mixing with a magnetic stirrer.

Paste B1

A composition containing 1.30 de-ionized water, 0.36 g tartaric acid, 3.26 g polyacid and 2.28 g quartz powder (surface treated) was prepared. A homogeneous mixture was obtained by mixing with a kneading machine.

Paste B2

A composition containing 1.30 de-ionized water, 0.36 g tartaric acid, 3.26 g polyacid and 2.28 g kaolin powder was prepared. A homogeneous mixture was obtained by mixing with a kneading machine.

Inventive Example 1

Paste A2 was intensely mixed with Paste B1 at a ratio of 1.5:1 by weight with a spatula. The time until the mixture was cured to a solid was observed. Testing specimens for flexural strength and compressive strength were prepared and stored in de-ionized water at 36° C. for 1 day before testing.

Inventive Example 2

Paste A3 was intensely mixed Paste B1 at a ratio of 1.5:1 by weight with a spatula. The time until the mixture was cured to a solid was observed. Testing specimens for flexural strength and compressive strength were prepared and stored in de-ionized water at 36° C. for 1 day before testing.

Inventive Example 3

Paste A4 was intensely mixed Paste B1 at a ratio of 1.5:1 by weight with a spatula. The time until the mixture was cured to a solid was observed. Testing specimens for flexural strength and compressive strength were prepared and stored in de-ionized water at 36° C. for 1 day before testing.

Inventive Example 4

Paste A1 was intensely mixed Paste B1 at a ratio of 1.5:1 by weight with a spatula. The time until the mixture was cured to a solid was observed. Testing specimens for flexural strength and compressive strength were prepared and stored in de-ionized water at 36° C. for 1 day before testing.

Inventive Example 5

Paste A2 was intensely mixed Paste B2 at a ratio of 1.5:1 by weight with a spatula. The time until the mixture was cured to a solid was observed. Testing specimens for flexural strength and compressive strength were prepared and stored in de-ionized water at 36° C. for 1 day before testing.

Comparative Paste A1

A composition containing 3.662 g de-ionized water, 0.333 g Levasil™ 300/30%, 0.005 g methyl cellulose and 6.000 g ionomer glass powder (Ketac™ Molar) was prepared. A homogeneous mixture was obtained by mixing with a magnetic stirrer.

Comparative Paste B1

A composition containing 3.733 g de-ionized water, 0.267 g Levasil™ 300/30%, 4.500 g polyacid and 1.500 g quartz powder was prepared. A homogeneous mixture was obtained by mixing with a magnetic stirrer.

Comparative Example 1

Comparative Paste A1 was intensely mixed with Comparative Paste B1 at a ratio of 3:1 by weight with a spatula. The time until the mixture cured to a solid was observed. Testing specimens for flexural strength and compressive strength were prepared and stored in de-ionized water at 36° C. for 1 day before testing.

Comparative Example 2

Comparative Paste A1 was intensely mixed with Comparative Paste B1 at a ratio of 2:1 by weight with a spatula. The time until the mixture cured to a solid was observed. Testing specimens for flexural strength and compressive strength were prepared and stored in de-ionized water at 36° C. for 1 day before testing.

Comparative Paste A2

A composition containing 0.36 g de-ionized water and 1.64 g ionomer glass powder (Ketac™ Molar) was prepared. A homogeneous mixture could not be obtained.

TABLE 1

|  | water [wt.-%] | tartaric acid [wt.-%] | polyacid [wt.-%] | filler A [wt.-%] | filler B [wt.-%] | filler C [wt.-%] | viscosity [Pa * s] | density [g/cm³] | pH value |
|---|---|---|---|---|---|---|---|---|---|
| Paste A1 | 12.5 | — | — | 12.5 | — | 75.0 | 436 | 2.4 | 7.2 |
| Paste A2 | 11.1 | — | — | 11.1 | — | 77.8 | 11680 | 2.3 | 7.3 |
| Paste A3 | 13.3 | — | — | 8.9 | — | 77.8 | 1303 | 2.4 | 7.5 |
| Paste A4 | 15.5 | — | — | 6.7 | — | 77.8 | 756 | 2.1 | 7.4 |
| Paste B1 | 18.0 | 5.0 | 45.3 | — | 31.7 | — | 15450 | 1.7 | 1.9 |
| Paste B2 | 18.0 | 5.0 | 45.3 | — | 31.7 | — | 11290 | 1.7 | 1.9 |
| Comparative Paste A1 | 39.0 | — | — | 1.0 | — | 60.0 | 1 | 1.4 | n.m. |
| Comparative Paste B1 | 39.2 | — | 45.0 | 0.8 | 15.0 | — | 11 | 1.5 | n.m. |
| Comparative Paste A2 | 18.0 | — | — | — | — | 72.0 | n.m. | n.m. | n.m. | n.m.: not measured

TABLE 2

|  | water content [wt.-%] | FS [MPa] | CS [MPa] |
|---|---|---|---|
| Inventive Example 1 | 13.9 | 37 | 217 |
| Inventive Example 2 | 15.2 | 26 | 187 |
| Inventive Example 3 | 16.6 | 30 | 219 |
| Inventive Example 4 | 14.7 | 31 | 209 |
| Inventive Example 5 | 13.9 | 38 | 207 |
| Comparative Ex. 1 | 39.1 | 2 | 14 |
| Comparative Ex. 2 | 39.1 | 5 | 22 |

Findings

The measured strength values of the inventive examples exceeded the values that can be obtained with state-of-the art compositions that contain more water.

During the mixing procedure, all inventive examples showed a good and easy mixability. The flowability was greatly improving during mixing.

The invention claimed is:

1. A kit of parts for preparing a glass ionomer composition for dental use, the kit comprising: a Paste A and a Paste B,
Paste A comprising:
water in an amount from 5 to 18 wt.-%;
an acid-reactive inorganic filler C in an amount from 20 to 90 wt.-%, the acid-reactive inorganic filler C having a mean particle size in the range from 3 to 10 μm and being selected from metal oxides, metal hydroxides, hydroxyapatite, aluminosilicate glasses, fluoroaluminosilicate glasses and mixtures thereof; and
a non acid-reactive filler A in an amount from 1 to 50 wt.-%, the non acid-reactive filler A having a mean particle size in the range from 10 nm to 500 nm and being selected from silica, alumina, titania, zirconia and mixtures thereof; and
Paste B comprising:
water in an amount from 7 to 20 wt.-%;
a polyacid in an amount from 3 to 70 wt.-%;
a complexing agent in an amount from 0.1 to 12 wt.-%; and
a non acid-reactive filler B in an amount from 5 to 60 wt.-%, the non acid-reactive filler B having a mean particle size in the range from 1 to 10 μm and being selected from quartz, kaolin, silica, alumina, titania, zirconia and mixtures thereof;
wt.-% with respect to the weight of the respective Paste A or Paste B,
wherein neither Paste A nor Paste B comprising polymerizable component(s) in an amount above 1 wt.-% with respect to the weight of the composition obtained when mixing Paste A and Paste B.

2. The kit of parts of claim 1, the water content of Paste A being lower than the water content of Paste B.

3. The kit of parts of claim 1, the non acid-reactive filler A being characterized by the following feature:
pH value of a dispersion of 1 g filler stirred in 10 ml de-ionized water for 5 minutes: between 4 and 7.

4. The kit of parts of claim 1, the non acid-reactive filler B being characterized by the following feature:
pH value of a dispersion of 1 g filler stirred in 10 ml de-ionized water for 5 minutes: between 4 and 7.

5. The kit of parts of claim 1, the acid-reactive inorganic filler C being characterized by the following feature:
pH value of a dispersion of 1 g filler stirred in 10 ml de-ionized water for 5 minutes: between 6 and 10.

6. The kit of parts of claim 1, the acid-reactive inorganic filler C the being selected from basic metal oxides, metal hydroxides, hydroxyapatite, aluminosilicate glasses, fluoroaluminosilicate glasses, glasses having a Si/Al ratio by wt.-% of below 1.5 and mixtures thereof.

7. The kit of parts of claim 6, Paste A being characterized by at least one or more of the following parameters:
viscosity: from 200 to 50,000 at 28° C., measured at a shear rate of 1 s$^{-1}$;
density: from 1.9 to 2.8 g/cm³;
pH value: from 7 to 10 determined with a pH electrode for 1 g Paste A dispersed in 10 ml de-ionized water and stirred for 5 minutes.

8. The kit of parts of claim 1, Paste B being characterized by at least one or more of the following parameters:
viscosity: from 1,000 to 50,000 at 28° C., measured at a shear rate of 1 s$^{-1}$;
density: from 1.5 to 2.0 g/cm³;
pH value: from 1 to 4 determined with a pH electrode for 1 g of Paste B dispersed in 10 ml de-ionized water and stirred for 5 minutes.

9. The kit of parts of claim 1, neither Paste A nor Paste B comprising at least one or more or all of the following components:
polymerizable component(s) in an amount above about 1 wt.-%;
initiator component(s) suitable to cure polymerizable component(s) in an amount above 1 wt.-%;
inhibitior(s) in an amount above 1 wt.-%;

desiccant(s) in an amount above 1 wt.-%, wt.-% with respect to the weight of the respective Paste A or Paste B.

10. A hardened composition for dental use, the hardened composition being obtainable by mixing Paste A and Paste B of the kit of parts described in claim 1 to obtain a mixture, and letting the mixture harden, the hardened composition being characterized by at least one or more of the following parameters:

Flexural strength: above 20 MPa determined according to EN-ISO 9917-2:2010;

Compressive strength: above 100 MPa determined according to EN-ISO 9917-1/2007.

11. A device for storing the kit of parts described in claim 1, the device comprising two compartments, Compartment A and Compartment B, Compartment A containing Paste A and Compartment B containing Paste B, Compartment A and Compartment B both comprising a nozzle or an interface for receiving an entrance orifice of a static mixing tip.

* * * * *

UNITED STATES PATENT AND TRADEMARK OFFICE
CERTIFICATE OF CORRECTION

PATENT NO. : 10,548,818 B2  
APPLICATION NO. : 15/745565  
DATED : February 4, 2020  
INVENTOR(S) : Jahns et al.

Page 1 of 2

It is certified that error appears in the above-identified patent and that said Letters Patent is hereby corrected as shown below:

In the Specification

Column 3  
Line 18, delete "i.a." and insert -- i.e., --, therefor.

Column 3  
Line 20, delete "unsatureated" and insert -- unsaturated --, therefor.

Column 3  
Line 38, delete "Paste B," and insert -- Paste B. --, therefor.

Column 4  
Line 55, delete "(i. e.," and insert -- (i.e., --, therefor.

Column 4  
Line 56, delete "(i. e.," and insert -- (i.e., --, therefor.

Column 7  
Line 35, delete "acid-reative" and insert -- acid-reactive --, therefor.

Column 13  
Line 49, delete "inhibitior(s)" and insert -- inhibitor(s) --, therefor.

Column 13  
Line 52, delete "zeolithe(s)" and insert -- zeolite(s) --, therefor.

Column 15  
Line 40, delete "thereof." and insert -- thereof, --, therefor.

Signed and Sealed this  
Fifteenth Day of September, 2020

Andrei Iancu  
*Director of the United States Patent and Trademark Office*

Column 16
Line 8 (approx.), delete "thereof." and insert -- thereof, --, therefor.

Column 17
Line 47, delete "harde n." and insert -- harden. --, therefor.

Column 18
Line 61, delete "foil;" and insert -- foil. --, therefor.

Column 19
Line 21, delete "Quantacrome)" and insert -- Quantachrome) --, therefor.

In the Claims

Column 24
Line 40 (approx.), in Claim 6, after "filler C" delete "the".

Column 24
Line 67, in Claim 9, delete "inhibitior(s)" and insert -- inhibitor(s) --, therefor.